United States Patent
Sial et al.

(10) Patent No.: US 10,682,126 B2
(45) Date of Patent: Jun. 16, 2020

(54) PHANTOM TO DETERMINE POSITIONAL AND ANGULAR NAVIGATION SYSTEM ERROR

(71) Applicants: SYNAPTIVE MEDICAL (BARBADOS) INC., Bridgetown (BB); Aisha Sial, Toronto (CA); Katlin Jean Kreamer-Tonin, Toronto (CA); Rajkumar Venkatesalu, Toronto (CA); Sean Jy-shyang Chen, Toronto (CA)

(72) Inventors: Aisha Sial, Toronto (CA); Katlin Jean Kreamer-Tonin, Toronto (CA); Rajkumar Venkatesalu, Toronto (CA); Sean Jy-Shyang Chen, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 484 days.

(21) Appl. No.: 15/518,365

(22) PCT Filed: May 11, 2016

(86) PCT No.: PCT/CA2016/050535
§ 371 (c)(1),
(2) Date: Apr. 11, 2017

(87) PCT Pub. No.: WO2017/193197
PCT Pub. Date: Nov. 16, 2017

(65) Prior Publication Data
US 2018/0185014 A1  Jul. 5, 2018

(51) Int. Cl.
*A61B 17/00* (2006.01)
*A61B 34/20* (2016.01)
(Continued)

(52) U.S. Cl.
CPC ............ *A61B 17/00* (2013.01); *A61B 34/20* (2016.02); *A61B 17/34* (2013.01);
(Continued)

(58) Field of Classification Search
CPC . A61B 17/00; A61B 34/20; A61B 2090/3937; A61B 2090/103;
(Continued)

(56) References Cited

U.S. PATENT DOCUMENTS 6,167,296 A * 12/2000 Shahidi .................... A61B 5/06
600/117
2014/0121501 A1  5/2014 Fichtinger et al.

FOREIGN PATENT DOCUMENTS

| EP | 2706913 | 3/2014 |
| WO | 2009152613 | 12/2009 |
| WO | 2016058078 | 4/2016 |

* cited by examiner

*Primary Examiner* — Katherine M Shi
*Assistant Examiner* — Michael G Mendoza
(74) *Attorney, Agent, or Firm* — Rowand LLP

(57) ABSTRACT

A phantom to determine navigational error in a surgical navigation system that tracks the location of an elongate tool having a tip and a shaft based on a plurality of fiducials attached to the elongate tool. The phantom includes a base portion that models a lower portion of a mammalian head and having a top surface with a plurality of touch points, each of the touch points being a respective indentation, and a frame detachably securable to the base portion and having an upper portion spaced apart from the top surface, the upper portion having defined therein a plurality of apertures. A tip of the elongate tool is to be inserted through said one of the apertures and in one of the touch points, and the surgical navigation system determines positional and angular error.

20 Claims, 8 Drawing Sheets

(51) Int. Cl.
*A61B 90/00* (2016.01)
*A61B 17/34* (2006.01)
*A61B 90/10* (2016.01)

(52) U.S. Cl.
CPC .............. *A61B 2017/00707* (2013.01); *A61B 2034/207* (2016.02); *A61B 2034/2055* (2016.02); *A61B 2090/103* (2016.02); *A61B 2090/3937* (2016.02); *A61B 2090/3983* (2016.02)

(58) Field of Classification Search
CPC .............. A61B 2034/207; A61B 17/34; A61B 2090/3983; A61B 2017/00707; A61B 2034/2055; A61B 2034/2068; A61B 2034/2072; A61B 34/10; A61B 2034/107; A61B 2034/108
See application file for complete search history.

PHANTOM TO DETERMINE POSITIONAL AND ANGULAR NAVIGATION SYSTEM ERROR

FIELD

The present application generally relates to image-guided medical procedures and navigation systems used to track objects in an image-guided medical procedure.

BACKGROUND

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimens, and radiation therapy are only a few examples of procedures utilizing imaging guidance in the medical field. Optical tracking systems, used during a medical procedure, track the position of a part of the instrument that is within line-of-site of the optical tracking camera. These optical tracking systems also require a reference to the patient to know where the instrument is relative to the target (e.g., a tumor) of the medical procedure.

Three dimensional (3D) sensor systems are increasingly being used in a wide array of applications, including medical procedures. These sensor systems determine the shape and/or features of an object positioned in a scene of the sensor system's view. In recent years, many methods have been proposed for implementing 3D modeling systems that are capable of acquiring fast and accurate high resolution 3D images of objects for various applications.

In clinical procedures, three dimensional sensor systems may be used to track the location of instruments. Tracking of instruments relative to the patient and the associated imaging data is also often achieved by way of external hardware systems such as mechanical arms, or radiofrequency or optical tracking devices. As a set, these devices are commonly referred to as surgical navigation systems.

Pre-operative imaging data such as Magnetic Resonance Imaging (MRI), Computerized Tomography (CT) and Positron Emission Tomography (PET), is integrated into the surgical room statically through a viewing station, or dynamically through a navigation system. The navigation system registers devices to a patient, and a patient to the pre-operative scans, allowing for instruments to be viewed on a monitor in the context of the pre-operative information.

Port-based surgery is a minimally invasive surgical technique where a port is introduced to access a surgical region of interest using surgical tools. Unlike other minimally invasive techniques, such as laparoscopic techniques, a port diameter is larger than a tool diameter. Hence, the tissue region of interest is visible through the port, wherein exposed tissue in a region of interest, at a depth few centimetres below the skin surface, is accessible through a narrow corridor in the port.

In order for a surgical navigation system to be reliably incorporated into surgical procedures, it needs to be shown to be sufficiently accurate in its ability to track objects in the system's field of view.

SUMMARY

The present application describes a kit for use in determining navigational error in a surgical navigation system. The kit includes an elongate tool having a tip and a shaft, the elongate tool to be tracked by the surgical navigation system based on a plurality of fiducials attached to the elongate tool. The kit also includes a phantom. The phantom includes a base portion that models a lower portion of a mammalian head and having a top surface with a plurality of touch points, each of the touch points being a respective indentation, and a frame detachably securable to the base portion and having an upper portion spaced apart from the top surface, the upper portion having defined therein a plurality of apertures. A tip of the elongate tool is to be inserted through said one of the apertures and in one of the touch points, and wherein the position of the tip and the angular trajectory of the shaft of the elongate tool is determinable by the surgical navigation system and then comparable to data regarding a measured position of said one of the touch points and a measured trajectory between said one of the touch points and said one of the apertures to determine positional and angular error.

In a first aspect, the present application describes method to determine navigational error in a surgical navigation system using a phantom having a base portion that models a lower portion of a mammalian head and having a top surface with a plurality of touch points, each of the touch points being a respective indentation, and the phantom including a frame detachably securable to the base portion and having an upper portion spaced apart from the top surface, the upper portion having defined therein a plurality of apertures. The method includes registering the phantom to determine a three-dimensional location of the phantom; inserting a tip of an elongate tool through one of the apertures and into one of the touch points, the elongate tool having a shaft and a plurality of fiducials; estimating, using the surgical navigation system, the position of the tip and the angular trajectory of the shaft of the elongate tool based on detecting the location of the plurality of fiducials; and determining positional and angular error by comparing the position of the tip and angular trajectory of the shaft estimated by the surgical navigation system with measured data regarding the location of said one of the touch points and said one of the apertures.

In another aspect, the present application discloses a phantom to determine navigational error in a surgical navigation system that tracks the location of an elongate tool having a tip and a shaft based on a plurality of fiducials attached to the elongate tool. The phantom includes a base portion that models a lower portion of a mammalian head and having a top surface with a plurality of touch points, each of the touch points being a respective indentation, and a frame detachably securable to the base portion and having an upper portion spaced apart from the top surface, the upper portion having defined therein a plurality of apertures. A tip of the elongate tool is to be inserted through said one of the apertures and in one of the touch points, and wherein the position of the tip and the angular trajectory of the shaft of the elongate tool is determinable by the surgical navigation system and then comparable to data regarding a measured position of said one of the touch points and a measured trajectory between said one of the touch points and said one of the apertures to determine positional and angular error.

Other aspects and features of the present application will be understood by those of ordinary skill in the art from a review of the following description of examples in conjunction with the accompanying figures.

In the present application, the term "and/or" is intended to cover all possible combination and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Other aspects and features of the present application will be understood by those of ordinary skill in the art from a review of the following description of examples in conjunction with the accompanying figures.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

Some embodiments of the present disclosure relate to minimally invasive medical procedures that are performed via an access port, whereby surgery, diagnostic imaging, therapy, or other medical procedures (e g minimally invasive medical procedures) are performed based on access to internal tissue through the access port. As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

An example of an access port is an intracranial conduit which may be employed in neurological procedures in order to provide access to internal tissue pathologies, such as tumors. One example of an intracranial access port is the BrainPath™ surgical access port provided by NICO, which may be inserted into the brain via an obturator with an atraumatic tip. Such an access port may be employed during a surgical procedure, by inserting the access port, via the obturator that is received within the access port, through the white and gray matter of the brain to access a surgical site.

Minimally invasive brain surgery using access ports is a recently conceived method of performing surgery on brain tumors previously considered inoperable. One object of the present invention is to provide a system and method to assist in minimally invasive brain surgery. To address intracranial surgical concerns, specific products such as the NICO BrainPath™ port have been developed for port-based surgery.

Figure 1:
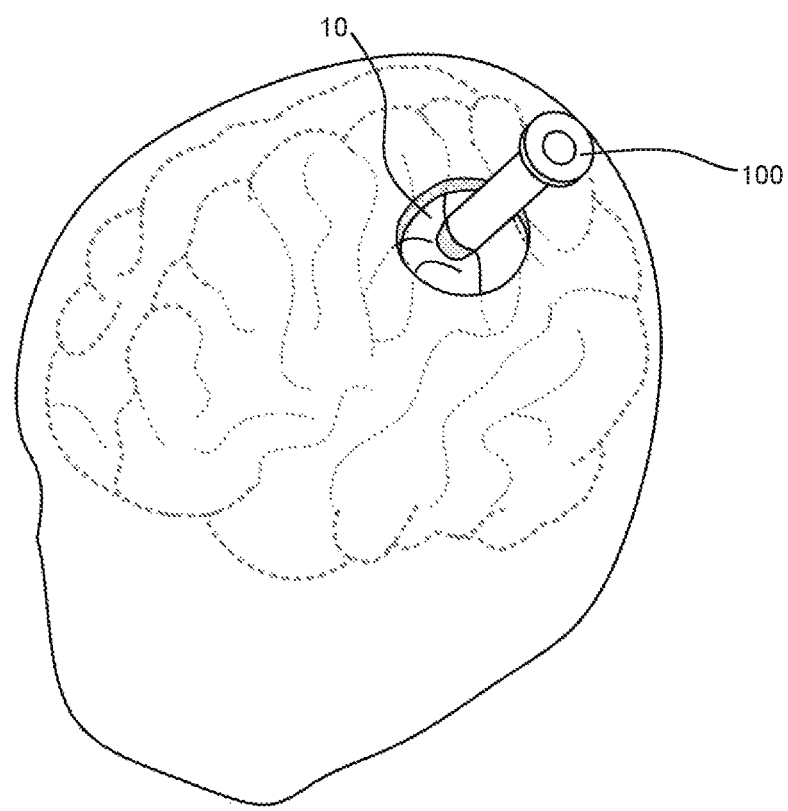
FIG. 1 illustrates the insertion of an access port into a human brain, for providing access to internal brain tissue during a medical procedure.

FIG. 1 illustrates the insertion of an access port 100 into a human brain 10, for providing access to internal brain tissue during a medical procedure. Surgical instruments (which includes any surgical equipment a surgeon may employ during a brain surgery including medical instruments such as scalpels, needles, biopsy probes, suctioning devices, scissors to mention just a few) may then be inserted within the lumen of the access port 100 in order to perform surgical, diagnostic and/or therapeutic procedures, such as resecting tumors as necessary.

As seen in FIG. 1, port 100 is comprised of a cylindrical assembly formed of an outer sheath. Port 100 may accommodate an introducer (not shown) which is an internal cylinder that slidably engages the internal surface of port 100. The introducer may have a distal end in the form of a conical atraumatic tip to allow for insertion into the sulcal folds of the brain 10. Port 100 has a sufficient diameter to enable bimanual manipulation of the surgical instrument(s) within its annular volume such as suctioning devices, scissors, scalpels, and cutting devices as examples.

Figure 2:
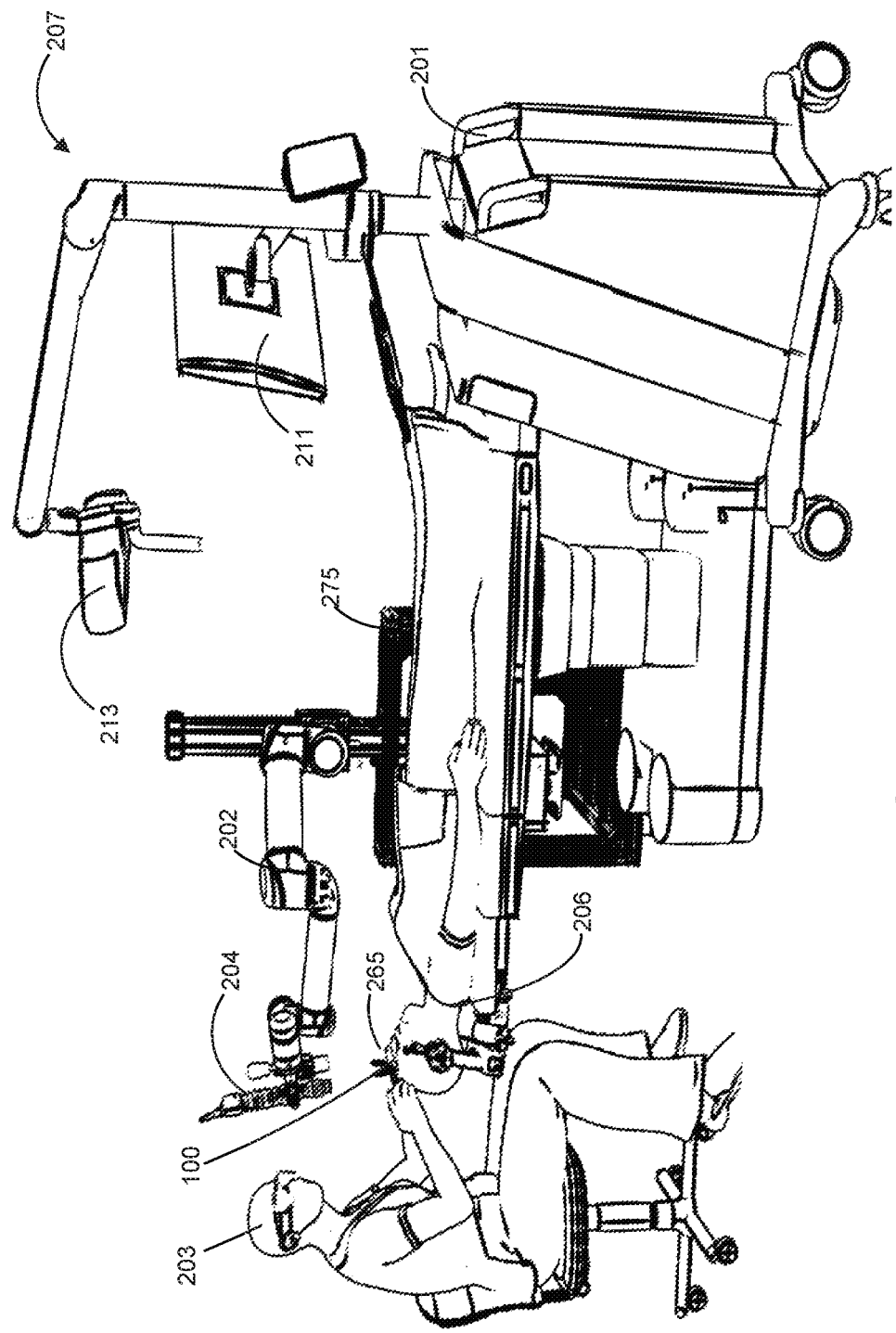
FIG. 2 is a diagram illustrating components of an exemplary surgical system used in port-based surgery.

FIG. 2 is a diagram illustrating components of an exemplary surgical system used in port-based surgery. FIG. 2 shows a navigation system 207 having an equipment tower 201, tracking system 213, display 211 (for a graphical user interface), an intelligent positioning system 275 and tracking markers 265 used to track surgical instruments or access port 100. Tracking system 213 tracks the tracking markers 265. It should be noted that all tracking systems may be employed to register objects into a coordinate space, such as the common coordinate space described below. Generally all systems which are used to register objects to a coordinate space employ a tracking system of some form, which is any system that may be used to acquire the coordinates of a landmark or object (collection of landmarks) in a coordinate space.

As shown in FIG. 2, surgeon 203 is resecting a tumor in the brain of a patient 206, through port 100. External scope 204, attached to automated arm 202, is typically used by the surgeon to enhance visibility of the brain at the distal end of the port 100. The external scope 204 may be zoomed-in or zoomed-out, and its output depicted on a visual display 211.

In practice surgical navigation systems are used to assist in guiding a surgeon to a surgical area of interest which is occluded by the surrounding anatomical tissue. For example a surgeon may want to access a deep seated tumor adjacent a patients ventricle, or spinal tumor located adjacent the spinal cord. In these cases common surgical procedures such as open surgery are more harmful than helpful in treating the patient. Thus non-invasive approaches are generally preferred. However non-invasive surgical procedures require a surgeon to traverse through patient tissue effectively blind. To reach the surgical area of interest a surgeon will generally use a 3D volumetric image of the patient such as an MRI or CT to identify a target they want to access to perform the surgical procedure on, they then choose an entry point at the surface of the patient and using the dimensional attributes of the image calculate a path to follow. However unlike following a path on a map, since the surgeon is traversing tissue using a solid tool, the surgeon cannot see where they are going. This is analogous to navigating the world blind with only a Braille map to tell you how far you should travel before changing course. Thus the trajectories once traversed are prone to error which can be detrimental to a patient's well-being. To address this problem surgical navigation systems provide a means of representing the location of a tracked tool relative to a patient's anatomy in order to assist the surgeon in ascertaining the position of that tool within the patient. This is accomplished by representing the position of the tool relative to the anatomy in the physical coordinate space of the operating room as the position of a virtual tool relative to a virtual anatomy in a common coordinate space as described herein. Where the position of the virtual tool relative to the virtual anatomy conserves the spatial relationship between their physical coordinate space counterparts.

One advantage of using a virtual representation of the physical operating room and more specifically a virtual representation of the surgeon operated tools relative to the patient, is the ability to more accurately ascertain the anatomical position of the tools within the patient at any given time during the surgical procedure. This advantage is enabled by the voxelated nature of the virtual space which allows access to cross sectional views of the patient anatomy including the location of the virtual tool which are occluded in physical space by the surrounding anatomy.

In use, a surgical navigation system detects surgical tools in the operating theatre and maps those tools to a common coordinate space together with a patient reference and image data. In some embodiments, this is accomplished through tracking, optically, fiducials (markers) arranged on the tool in a unique pattern or geometry. The surgical navigation system locates the fiducials in the physical space and, from that data, is able to determine the position of the tool itself based upon stored data relating the tool geometry to the geometric arrangement of the fiducials. Using transforms, the coordinates of the tool and/or fiducials is then translated into the common coordinate space to which the patient's position is mapped, and to which pre-operative image data may be mapped. In this manner, the position of the tool relative to the patient, and image data obtained regarding the patient, are aligned and capable of being displayed to aid the surgeon during a surgical procedure.

To be effective, the surgical navigation system needs to be capable of accurately determining the location of a tracked object. To demonstrate or test the accuracy of a navigation system, the navigation system is used to determine the location of an object and that determination is compared to the actual or true location of the object. In the case of a surgical navigation system, accuracy may be tested by comparing the actual location of a physically tracked tool with the estimated location of the virtual tool as determined by the navigation system.

The present application, in one aspect, provides devices and methods for determining both the positional and angular error associated with a tool tracked by a navigational system. Positional error refers to the Euclidean distance between the location of a point on the physical tool and the corresponding point on the virtual tool. In the case of an elongate tool, the point being tracked may be the tip of the tool. However, any point on the tool may be used for determining positional error. Angular error refers to a difference in angular position between a line on the physical and the corresponding line on the virtual tool. For example, with an elongate tool, the "line" may be the longitudinal axis of a shaft or other elongate feature on the tool.

Figures 3, 4:
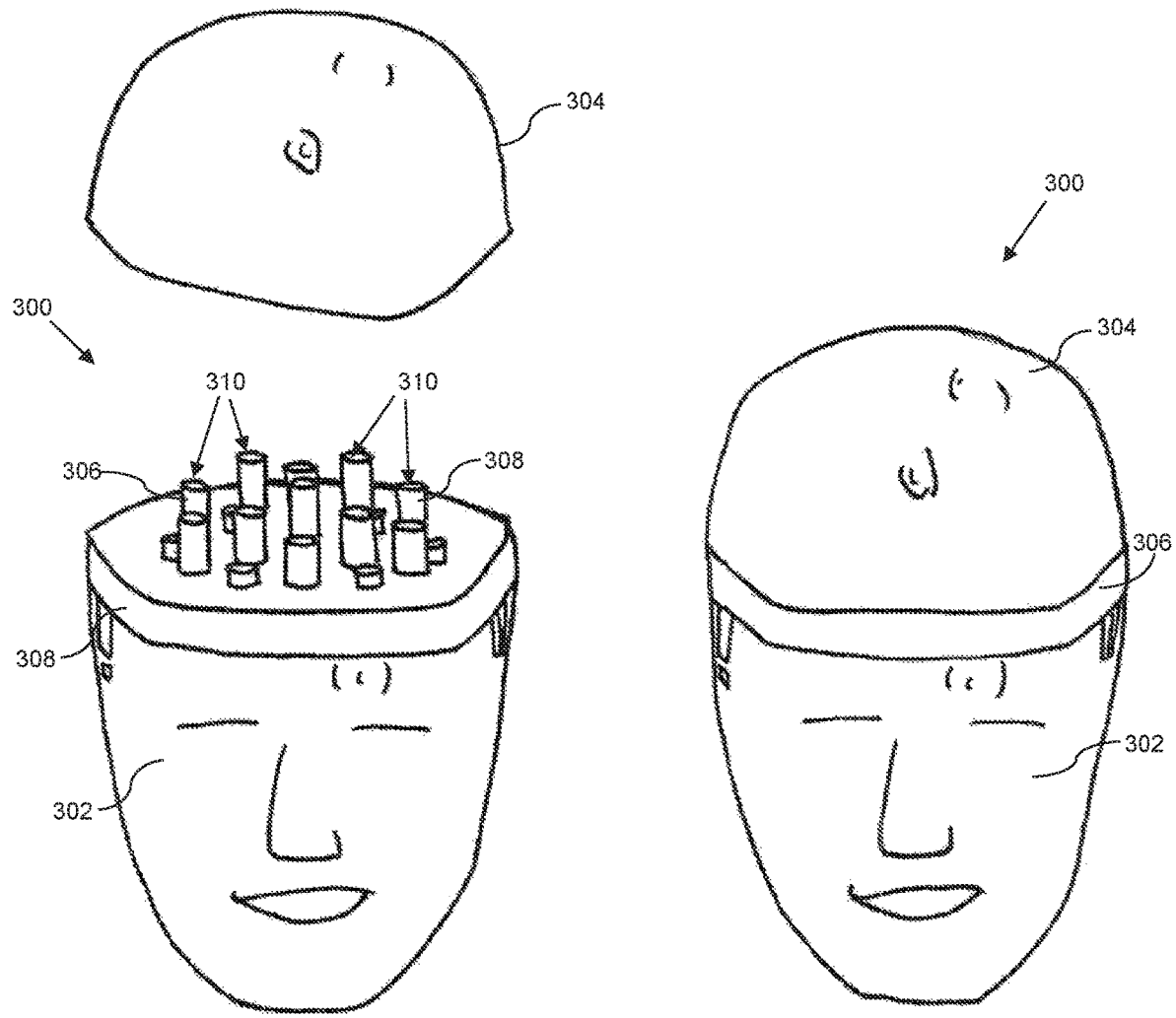
FIG. 3 shows an example embodiment of a phantom for determining accuracy of a surgical navigation system.
FIG. 4 shows the example phantom with the skull cap removed.

In one aspect, the present application provides a device and kit for assessing accuracy of a surgical navigational system. Reference is now made to FIG. 3, which shows an example embodiment of a phantom 300 for determining accuracy of a surgical navigation system. A phantom is an object used to mimic or model the subject of the surgical procedure. In this example case, where the operation involves neurosurgery, the phantom 300 is formed to model a mammalian (in this case, human) head. By adopting a shape similar to that of the actual real world subject of the surgery (a human head in this example) the conditions for testing accuracy more effectively model the real operating environment, for example by involving the usual patient registration procedure. The portion of the mammalian head included in the phantom may include prominent facial structures and features that are useful in registration (e.g. using surface trace registration, rapid registration, etc.).

The phantom 300 may include a base portion 302, which in this case includes most of the face and the base of the skull, and a skull cap 304. The skull cap 304 fits upon the base portion 302 and is detachable. The base portion 302 includes a top surface 306. In this example, the top surface 306 (shown in grey) is a physically separate part of the phantom 300 and is detachable from the base portion 302. In some embodiments, the top surface 306 may be integrally formed with the base portion 302; however, having a detachable top surface 306 will allow for the top surface 306 to be changed to provide for different functions, as will be elaborated upon below, or to allow the base portion to be used for purposes other than for accuracy testing.

Reference is now also made to FIG. 4, which shows the phantom 300 with the skull cap 304 removed. In this example embodiment, the top surface 306 includes a plurality of upwardly extending posts 308 or cylinders. Each post 308, in this example, is cylindrical and features a circular flat end having an indentation 310 formed therein. That is, each post 308 provides a touch point formed from the respective indentation 310 in that post 308. A "touch point" for the purposes of this description is a well-defined location used in positional and angular accuracy testing. A touch point formed as an indentation is a well-defined point to which an operating can position an end of a tracked object, in particular the tip of an elongate tool. In some examples, the upwardly extending posts 308 may be shapes other than cylindrical. In some cases, one or more of the posts 308 may be integrally formed or joined such that they appear as one upwards projection having two or more touch points (indentations 310) formed on their upper surface. In one example, the posts 308 are a continuous surface of varying height (e.g. elevation). In some embodiments, the top surface 306 may not feature any posts 308 and may be a substantially flat surface with a plurality of indentations 310 that form the plurality of touch points. Other variations will be apparent to those skilled in the art having regard to the description herein.

Figure 5:
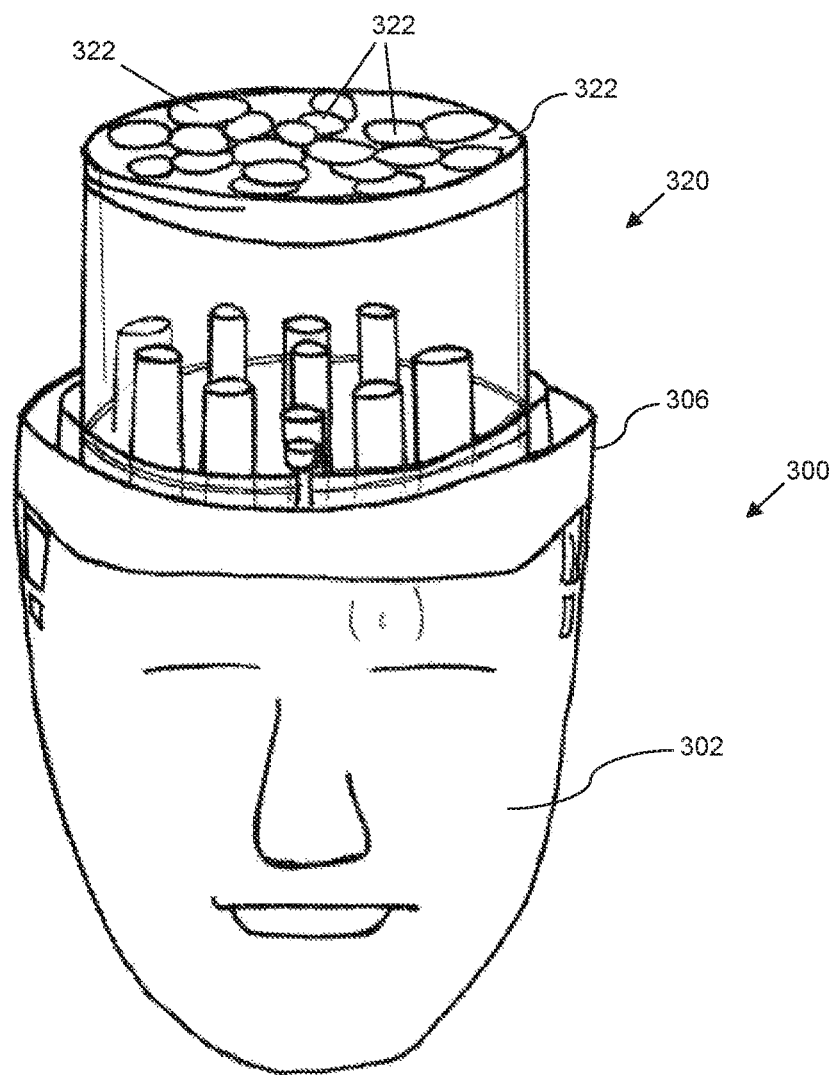
FIG. 5 shows the example phantom with a frame attached thereto.

Reference is now made to FIG. 5, which shows the phantom 300 with a frame 320 attached thereto. The frame 320 may be mechanically secured to the top surface 306 using clips, screws, clamps, or other mechanical fasteners.

The frame 320 and top surface 306 may be formed with cooperating physical features to ensure that the frame 320 is reliably repositionable in exactly the same relation to the top surface 306 each time it is attached.

The frame 320 includes an upper portion 322 spaced apart from the top surface 306. In this example, the frame 320 includes a circular upper portion 322 and a solid downwardly-projecting side wall to space the upper portion 322 from the top surface 306. The upper portion 322 in this example is a circular plate of generally uniform thickness. In other examples, the upper portion 322 need not be circular. In some examples, the frame 320 may feature two or more downwardly depending members or walls to support the upper portion 322.

The upper portion 322 of the frame 320 includes a plurality of apertures 324. The apertures 324 are sized to permit insertion of an elongate tool. In this example embodiment, the apertures 324 have at least a partly conical or funnel shape such that the portion of the aperture 324 closest to the top surface 306 is the narrowest diameter portion of the aperture 324. This may provide some flexibility in the angular positioning of the elongate tool when inserted through the aperture despite the thickness of the upper portion 322 and the relatively small size of the narrowest diameter part of the aperture 324.

Figure 6:
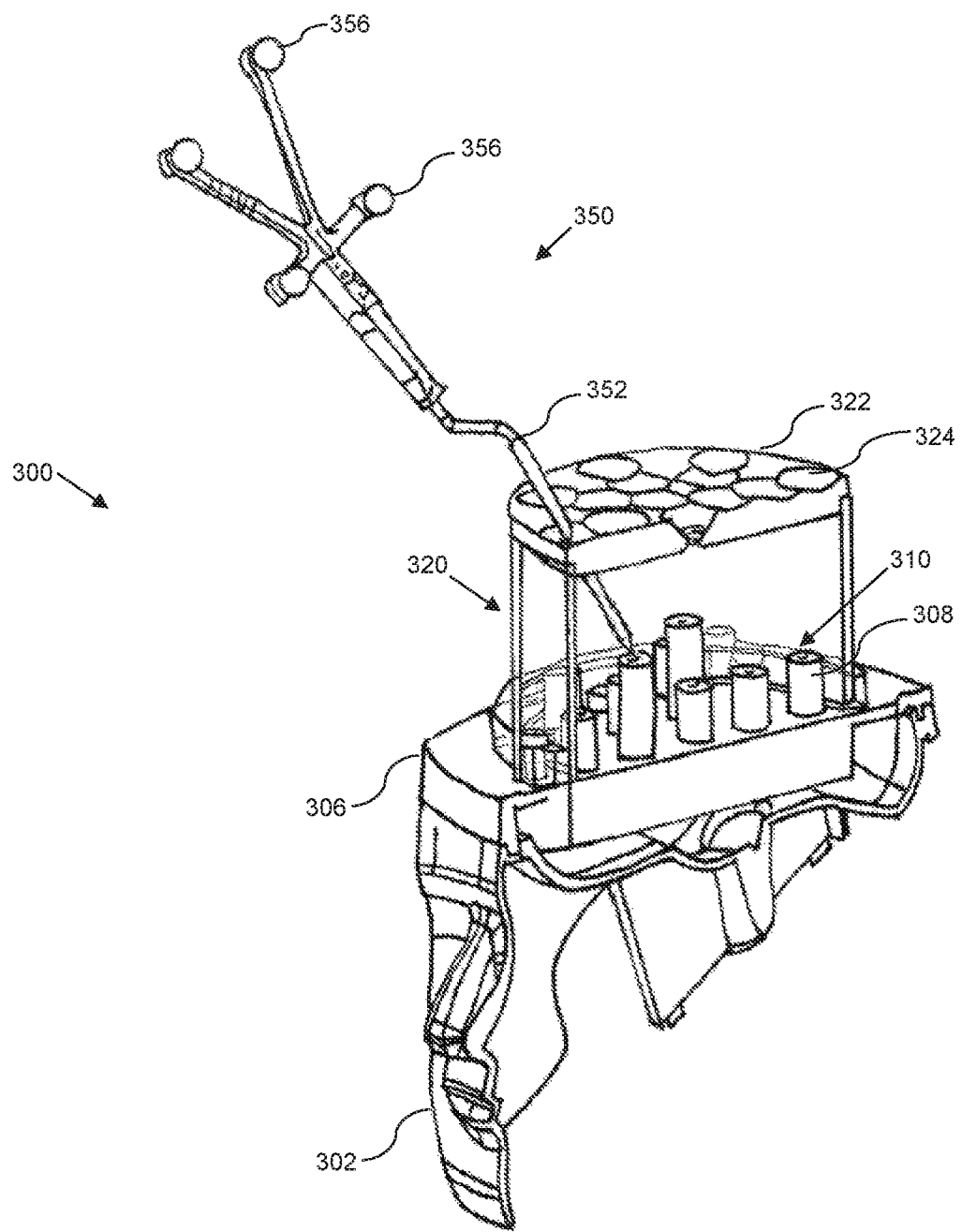
FIG. 6 shows a perspective cross-sectional view of the example phantom with an elongate tool.

Reference will now be made to FIG. 6, which shows a perspective cross-sectional view of the example phantom 300 with an elongate tool 350. In this example, the elongate tool 350 is a pointer tool having a shaft 352 with a pointed tip. The elongate tool 350 includes a plurality of fiducials 356 mounted to the elongate tool 350 in a fixed geometric pattern to enable tracking of the elongate tool 350 by the surgical navigation system.

The tip of the shaft 352 of the elongate tool 350 has been inserted through one of the apertures 324 and placed at one of the touch points, i.e. an indentation 310. With the tip of the elongate tool 350 in one of the indentations 310 and the shaft 352 extending to that touch point through one of the apertures 324, the surgical navigational system is then used to determine the location of the tip of the tool 350 and the angular position of its shaft 352 in relation to the position of the phantom 300. This determination is then compared with known or "truth" data regarding the position of the particular indentation 310 (touch point) and the vector extending from that touch point to the aperture 324 through which the tool was inserted. On this basis, positional error and angular error may be determined by the system.

Figure 7:
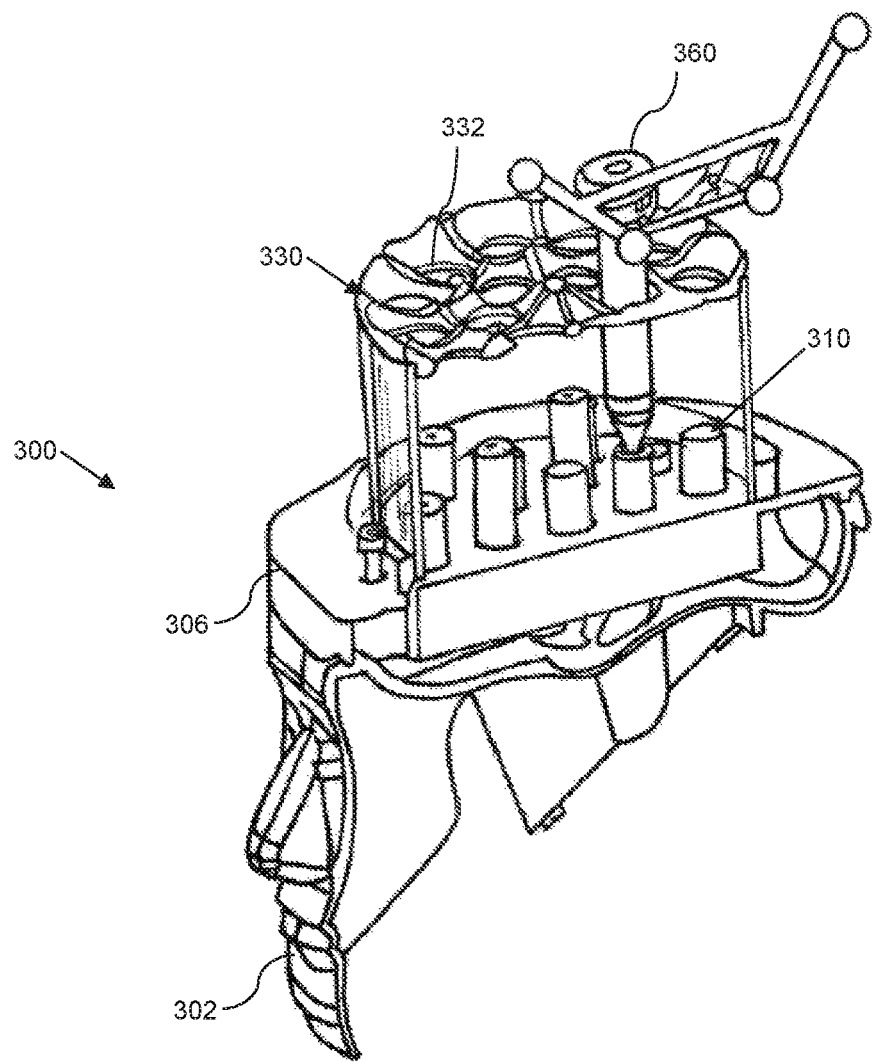
FIG. 7 shows, in perspective cross-section, another example embodiment of the phantom with a different elongate tool.

FIG. 7 shows, in perspective cross-section, another example embodiment of the phantom 300 with a different elongate tool. In this example, the phantom 300 includes another frame 330 having apertures 332 sized to allow insertion of an access port 360. The access port 360 has a significantly wider shaft portion. In this example embodiment, the apertures 332 on the frame 330 may be positioned so as to line up vertically with respective corresponding indentations 310, such that the access port 360 is inserted substantially perpendicularly to the upper portion of the frame 330 and the top surface 306.

Figure 8:
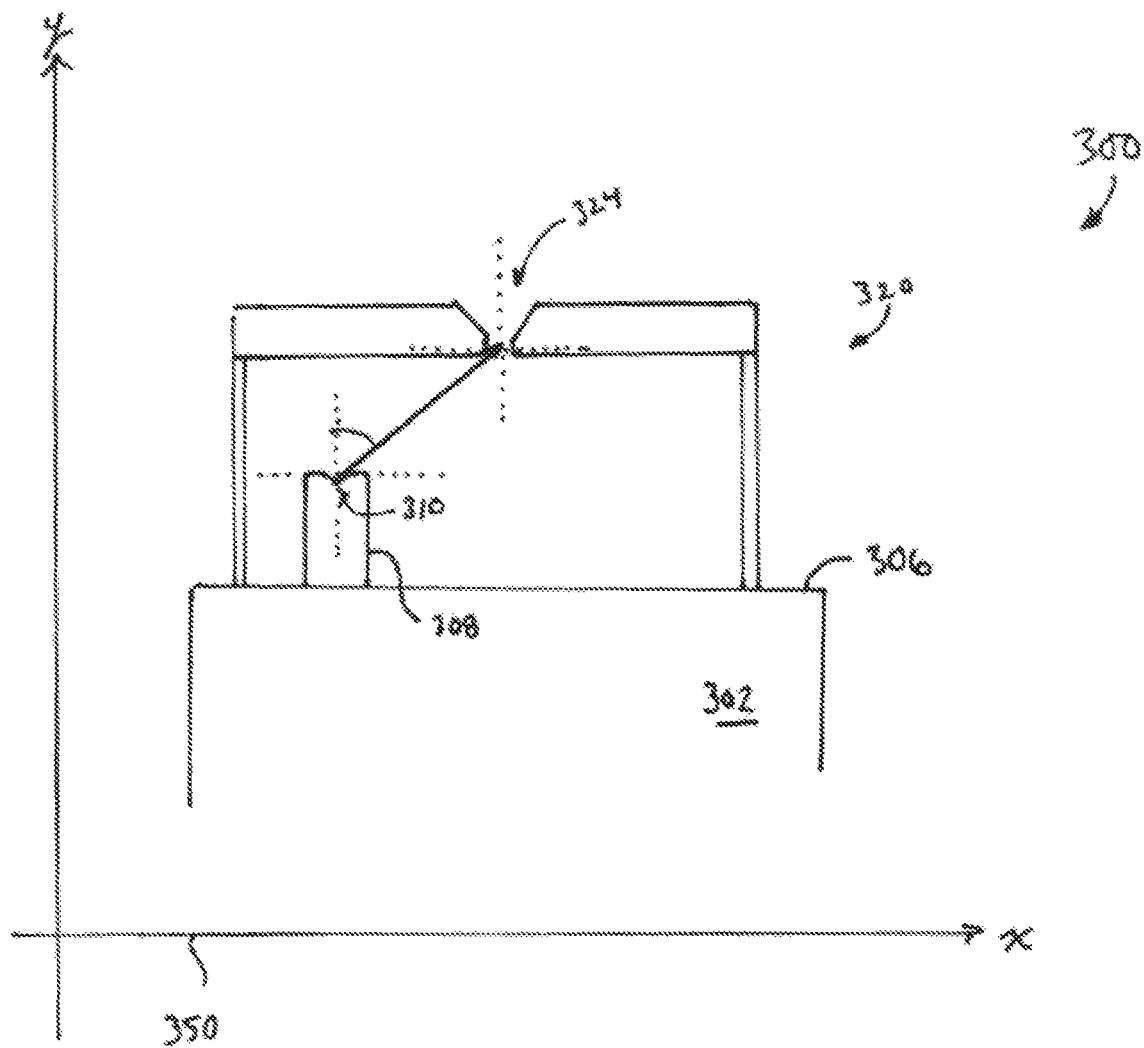
FIG. 8 shows a cross-sectional view of a frame and post portion of the phantom.

Reference is now made to FIG. 8, which shows a cross-sectional view of a portion of the phantom 300. For ease of illustration a single post 308 and indentation 310 are shown, and a single aperture 324 in the upper portion 322 is shown. As will be described below, through an initial registration process the "truth" data on the location of the phantom 300, i.e. the base portion 302 and the frame 320, is determined. The measured position of the phantom 300 is transformed or mapped to a virtual coordinate space, as indicated by reference numeral 350. Although FIG. 8 shows only x-y axes, it will be appreciated that the virtual coordinate space is a three-dimensional space.

The position of the phantom 300, and in particular the indentations 310 and the apertures 324, in the virtual coordinate space is "known" from the measured "truth" data.

To measure the accuracy of a surgical navigation system, an elongate tool is inserted through the aperture and the tip is placed in the indentation. The surgical navigation system is then used to identify the location of the elongate tool and, in particular, the location of its tip and the angle (in three-dimensions, e.g. the angle with respect to the y-axis and the z-axis) of the shaft projecting from the tip. The location of the tool tip and its angular trajectory is mapped to the virtual coordinate space.

From the measured three-dimensional locations of the indentations 310 and apertures 324, the system is able to determine the vector (i.e. trajectory) between pairs of indentations 310 and apertures 324 and, thus, the three-dimensional angle between them. The center of the lowest point in the aperture 324 may be used in determining the vector.

The location of the tool tip and its angle determined by the surgical navigation system is then comparable to the measured location of the corresponding indentation 310 into which the tool was placed. This give a measurement of positional error. In some embodiments Euclidean distance between the "true" location and the navigation system's estimated location may be used as the error measurement. Angular error may be determined from the difference between the calculated angle of a vector from the indentation 310 to the aperture 324 and the angle of the tool estimated by the navigation system.

The frame 320 with suitably-sized apertures 324 spaced apart from the touch point indentations 310 serves to create a measurable trajectory position into which an elongate tool may be placed so as to measure angular error.

Measurement of the Phantom

"Truth" data regarding the geometric properties of the phantom is obtained in some embodiments using a co-ordinate measuring machine (CMM) tool. Some CMM tools have a probe with an articulated arm and highly-accurate joint measurements to track the physical location of the tip of the probe. In this manner, the CMM tool is able to determine the physical characteristics of an object with a high degree of accuracy. Some CMM tools are laser-based non-contact measuring tools. In one example, the CMM is able to determine single point accuracy to better than 0.01 mm.

The CMM tool may be used to gather truth data regarding the physical properties of the phantom. In particular, the CMM tool measures the relative positions of a set of fiducial markers on the phantom, which may later be used during registration of the phantom. The CMM tool also measures the location of each indentation and each aperture in the frame(s).

In some embodiments, for example where surface contour-based registration may be used, a scan of the phantom may be taken. In order to create a scan where the phantom appears solid, a Digital Imaging and Communications in Medicine (DICOM) image series is created from a solid model of the accuracy phantom. The solid model of the accuracy phantom may be generated from a 3D scan taken by a CMM laser and given a false bottom in order to appear solid. A surface mesh may be extracted from the solid model and converted to a DICOM series with a 1 mm slice thickness, for example. The co-ordinate space of the solid model is preserved in the mesh, and is also preserved when converting the mesh into a DICOM series. This means that the solid model and the DICOM series are in the same co-ordinate space, which will be referred to as DICOM space. The DICOM space may be, in some embodiments, the virtual coordinate space referred to above. This DICOM series is not used as truth data when measuring the system accuracy.

Since the DICOM series and CMM truth data exist in separate co-ordinate spaces (DICOM space and CMM space respectively), a transform may co-register the two spaces. The process of co-registering the two spaces may be achieved using a least squares rigid registration algorithm in some examples. This algorithm registers the fiducials found in CMM space to the fiducials located in DICOM space and produces a transformation matrix. This transformation is then applied to the target and engagement point truth data sets to bring them from CMM space into DICOM space.

Accuracy Testing

To measure surgical navigation system accuracy, the phantom is first registered. Registration may be carried out through, for example, touch point registration or surface contour-based registration (e.g. surface trace registration, rapid registration, etc.). The registration process is intended to mimic the steps commonly used for registering a patient in a clinical procedure.

Once the phantom has been registered and a frame attached (with the skull cap removed), the navigated elongate tool, with tracking fiducials attached, is inserted through one of the apertures and its tip is placed in one of the indentations. Measurements are then taken by the surgical navigation system. The system may compare the estimated location and angle of the tool with the truth data in memory. The tool may be repositioned into different apertures and indentations so as to test a variety of trajectories and locations.

Figure 9:
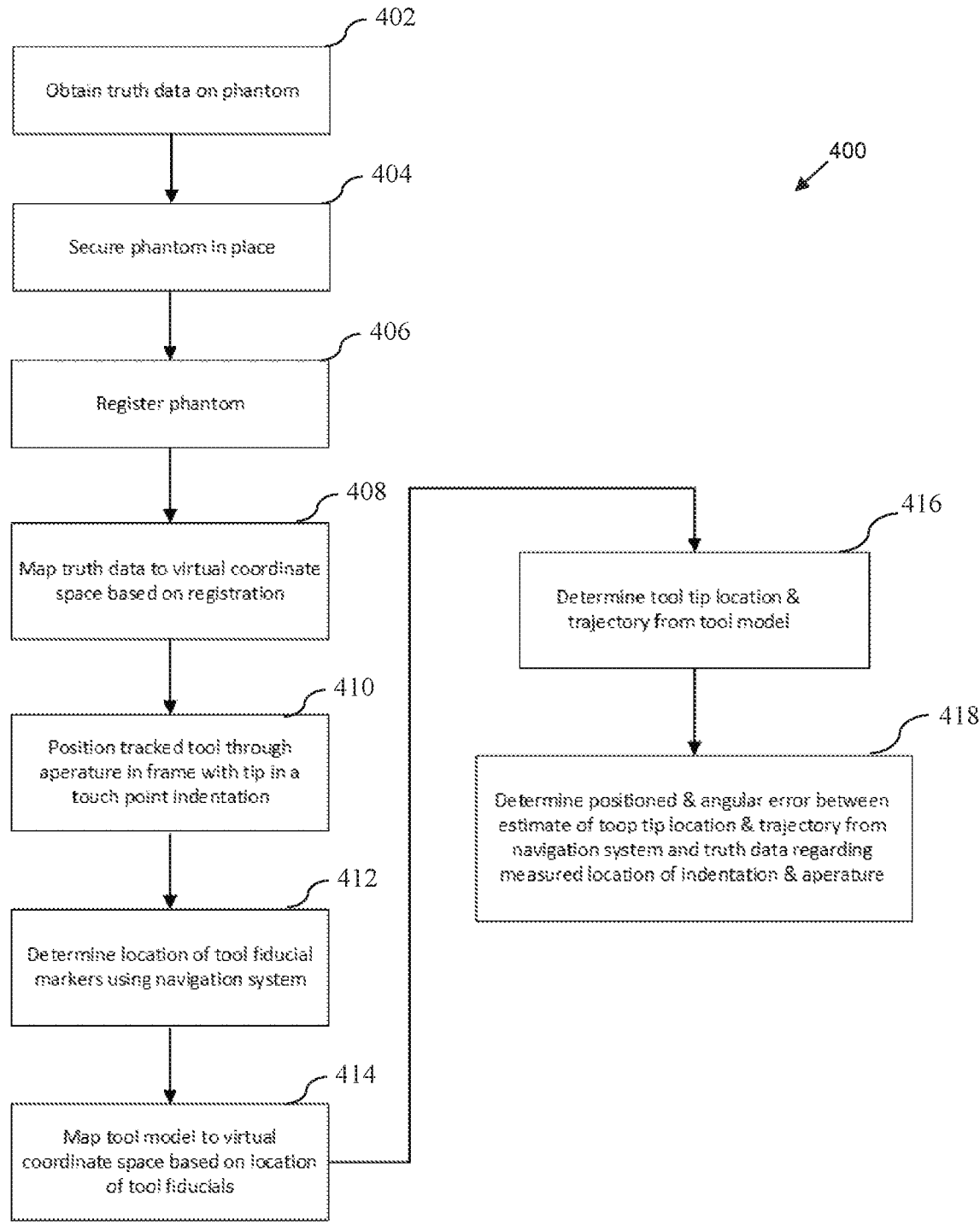
FIG. 9 shows, in flowchart form, an example method of measuring accuracy of a surgical navigation system.

Reference is now made to FIG. 9, which shows, in flowchart form, one example method 400 of measuring accuracy of a surgical navigation system. The method 400 uses a phantom, such as the example phantom described above.

In operation 402, "truth data" regarding the actual physical geometric properties of the phantom is obtained through measurement. As noted above, a CMM tool may be used in some embodiments to obtain the "truth data". The truth data, stored in memory, defines the physical geometric relationship between registration points on the phantom and, at least, touch point indentations on the phantom and apertures in the frame when attached to the base portion of the phantom. This truth data may be stored in a DICOM system, in some embodiments. Operation 402 may be performed by a manufacturer of the phantom in some embodiments and the measured "truth data" distributed together with the phantom to which it relates.

To measure the accuracy of a surgical navigation system, in operation 404 the phantom is first secured in place in a position. In some embodiments, the method 400 is at least partly carried out in an operating theatre so as to model the real-world circumstances in which the systems are used. The phantom may be secured using, for example, head clamps or other devices intended to render a patient's head immobile during surgery.

In operation 406, the phantom is registered. Registration may include touch point registration, in which pre-defined touch points on the phantom are located using a pointer tool and readings are taken to define the location of the phantom in a coordinate space. In some cases, registration may include surface trace registration. Irrespective of the methodology used, the registration of the phantom involves mapping its physical location to the virtual coordinate space.

In operation 408, the truth data is mapped to the virtual coordinate space based on the registration. For example, correlation between touch points detected during registration and the corresponding touch points in the truth data may be the basis for mapping the truth data to the virtual coordinate space using a suitable transform.

The surgical navigation system under test is configured to track the location of an elongate tool. The elongate tool includes a plurality of fiducial markers that enable the navigation system to estimate its location in three-dimensional space. For example, with an optical navigation system, the tool may feature a geometric pattern of reflective fiducial markers/spheres. Using stereoscopic cameras, the optical navigation system locates the markers in images and, from the location of the markers in pairs of contemporaneously obtained images, the system is able to determine the three-dimensional position of the geometric pattern of fiducial markers.

In operation 410, the elongate tool is inserted through an aperture in the frame attached to the base portion of the phantom and the tip of the elongate tool is placed in one of the touch point indentations on the upper surface of the based portion, thereby positioning the tip of the tool at the location of an indentation and its shaft at a trajectory extending from the indentation to the aperture.

Using the surgical navigation system, the location of the fiducial markers on the tool is determined in operation 412. Then in operation 414, a three-dimensional model of the tool and its markers is mapped to the virtual coordinate space based on mapping the estimated location of the fiducial markers determined by the navigation system. The estimated location of the tip of the tool and the trajectory of its shaft is then determined from the tool model in the virtual coordinate space, as indicated by operation 416.

In operation 418, the positional and angular error is determined by comparing the tool tip location and shaft trajectory estimated by the surgical navigation system with the indentation location and vector to the aperture defined by the truth data. Data from multiple readings and positions may be averaged to produce an average positional and angular error.

Certain adaptations and modifications of the described embodiments can be made. Therefore, the above discussed embodiments are considered to be illustrative and not restrictive.

What is claimed is:

1. A kit for use in determining navigational error in a surgical navigation system in a medical procedure, the kit comprising:
    an elongate tool having a tip and a shaft, the elongate tool to be tracked by the surgical navigation system based on a plurality of fiducials attached to the elongate tool; and
    a phantom including,
        a base portion that models a lower portion of a mammalian head and having a top surface with a plurality of touch points, each of the touch points being a respective indentation, and
        a frame detachably securable to the base portion and having an upper portion spaced apart from the top surface, the upper portion having defined therein a plurality of apertures,
        whereby a tip of the elongate tool is to be inserted through said one of the apertures and in one of the touch points, and wherein the position of the tip and the angular trajectory of the shaft of the elongate tool is determinable by the surgical navigation system and then comparable to data regarding a measured position of said one of the touch points and a measured trajectory between said one of the touch points and said one of the apertures to determine positional and angular error.

2. The kit claimed in claim 1, wherein the elongate tool comprises a pointer or an access port.

3. The kit claimed in claim 1 or claim 2, wherein said top surface includes a plurality of upwardly projecting posts, each post having an end including one of the respective indentations.

4. The kit claimed in claim 3, wherein at least two of the posts are of different heights to provide indentations at different elevations.

5. The kit claimed in any one of claims 1 to 4, wherein the upper portion comprises a plate, and wherein the frame includes at least one downwardly projecting side wall to hold said plate in spaced relation to said top surface.

6. The kit claimed in claim 5, wherein the apertures are conical.

7. The kit claimed in claim 6, wherein a narrowest diameter of each conical aperture in the plate is located at the side of the plate closest to the upper surface.

8. The kit claimed in any one of claims 5 to 7, wherein the plate is circular.

9. The kit claimed in any one of claims 1 to 8, wherein the fiducials comprise reflective markers, and wherein the surgical navigation system comprises an optical navigation system.

10. A method to determine navigational error in a surgical navigation system in a medical procedure using a phantom having a base portion that models a lower portion of a mammalian head and having a top surface with a plurality of touch points, each of the touch points being a respective indentation, and the phantom including a frame detachably securable to the base portion and having an upper portion spaced apart from the top surface, the upper portion having defined therein a plurality of apertures, the method comprising:
registering the phantom to determine a three-dimensional (3D) location of the phantom;
inserting a tip of an elongate tool through one of the apertures and into one of the touch points, the elongate tool having a shaft and a plurality of fiducials;
estimating, using the surgical navigation system, the position of the tip and the angular trajectory of the shaft of the elongate tool based on detecting the location of the plurality of fiducials; and
determining positional and angular error by comparing the position of the tip and angular trajectory of the shaft estimated by the surgical navigation system with measured data regarding the location of said one of the touch points and said one of the apertures.

11. The method claimed in claim 10, further comprising obtaining said measured data using a coordinate measuring machine tool.

12. The method claimed in claim 10 or claim 11, wherein estimating comprises determining an estimated location of the fiducial markers, mapping the fiducial markers to a virtual coordinate space, and mapping a model of the elongate tool to the virtual coordinate space based on the mapping of the fiducial markers.

13. The method claimed in any one of claims 10 to 12, further comprising repeating the inserting, estimating and determining operations for a plurality of different aperture and touch point combinations, and further determining an average positional and angular error.

14. A phantom to determine navigational error in a surgical navigation system that tracks the location of an elongate tool having a tip and a shaft based on a plurality of fiducials attached to the elongate tool, the phantom comprising:
a base portion that models a lower portion of a mammalian head and having a top surface with a plurality of touch points, each of the touch points being a respective indentation, and
a frame detachably securable to the base portion and having an upper portion spaced apart from the top surface, the upper portion having defined therein a plurality of apertures,
whereby a tip of the elongate tool is to be inserted through said one of the apertures and in one of the touch points, and wherein the position of the tip and the angular trajectory of the shaft of the elongate tool is determinable by the surgical navigation system and then comparable to data regarding a measured position of said one of the touch points and a measured trajectory between said one of the touch points and said one of the apertures to determine positional and angular error.

15. The phantom claimed in claim 14, wherein said top surface includes a plurality of upwardly projecting posts, each post having an end including one of the respective indentations.

16. The phantom claimed in claim 15, wherein at least two of the posts are of different heights to provide indentations at different elevations.

17. The phantom claimed in any one of claims 14 to 16, wherein the upper portion comprises a plate, and wherein the frame includes at least one downwardly projecting side wall to hold said plate in spaced relation to said top surface.

18. The phantom claimed in claim 17, wherein the apertures are conical.

19. The phantom claimed in claim 18, wherein a narrowest diameter of each conical aperture in the plate is located at the side of the plate closest to the upper surface.

20. The phantom claimed in any one of claims 17 to 19, wherein the plate is circular.

\* \* \* \* \*